United States Patent [19]

Bambury et al.

[11] Patent Number: 5,510,442
[45] Date of Patent: Apr. 23, 1996

[54] ORGANOSILICON-CONTAINING MATERIALS USEFUL FOR BIOMEDICAL DEVICES

[75] Inventors: Ronald E. Bambury, Fairport; Jay F. Kunzler, Canandaigua, both of N.Y.

[73] Assignee: Bausch & Lomb Incorporated, Rochester, N.Y.

[21] Appl. No.: 439,215

[22] Filed: May 11, 1995

Related U.S. Application Data

[62] Division of Ser. No. 45,459, Apr. 8, 1993.

[51] Int. Cl.$^6$ .................................................. C08G 77/04
[52] U.S. Cl. ................................ 528/28; 528/29; 528/41; 556/419; 556/421; 556/438
[58] Field of Search .................................. 528/28, 29, 41; 556/419, 421, 438

[56] References Cited

U.S. PATENT DOCUMENTS

| | | | |
|---|---|---|---|
| 3,408,429 | 10/1968 | Wichterle | 264/1 |
| 3,660,545 | 5/1972 | Wichterle | 264/1 |
| 4,113,224 | 9/1978 | Clark et al. | 249/105 |
| 4,122,074 | 10/1978 | Pepe et al. | 526/26 |
| 4,197,266 | 4/1980 | Clark et al. | 264/1 |
| 4,555,732 | 11/1985 | Tuhro | 358/213 |
| 4,686,267 | 8/1987 | Ellis et al. | 526/245 |
| 4,910,277 | 3/1990 | Bambury et al. | 526/260 |
| 5,034,461 | 7/1991 | Lai et al. | 525/100 |
| 5,070,215 | 12/1991 | Bambury et al. | 556/418 |
| 5,243,010 | 9/1993 | Choi et al. | 528/28 |

FOREIGN PATENT DOCUMENTS

| | | | |
|---|---|---|---|
| 0400613 | 12/1990 | European Pat. Off. | C08G 77/445 |
| 4208005 | 9/1992 | Germany | C08G 69/42 |

OTHER PUBLICATIONS

"A General Allylation Procedure Using Trimethylallylsilane and Fluoride Catalysts," by G. Majetich, A. Casares, D. Chapman, M. Behnke, *J. Org. Chem.*, vol. 51 (10), 1986, pp. 1745 et seq.

De Jose, et al., *Chem. Abstracts* 113 (7): 59276z.

*Chem. Abstracts* 101 (1): 7425e.

*Chem. Abstracts* 96 (5): 35532j.

*Primary Examiner*—Melvyn I. Marquis
*Attorney, Agent, or Firm*—John E. Thomas; Salvatore P. Pace

[57] ABSTRACT

Organosilicon-containing materials are useful in articles such as biomedical devices, including contact lenses. The materials include macromonomers endcapped with at least one ethylenically unsaturated radical, and monomers. The macromonomers and monomers include units of the formula:

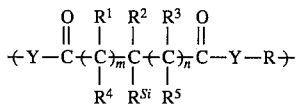

wherein:

each Y is —O— or —NR$^{30}$— wherein R$^{30}$ is H or C$_1$–C$_6$ alkyl;

each R$^1$, R$^2$, R$^3$, R$^4$ and R$^5$ is independently selected from the group consisting of H, C$_1$–C$_6$ alkyl, C$_1$–C$_6$ haloalkyl, C$_2$–C$_6$ alkyl wherein at least one methylene group is replaced with —O—, C$_2$–C$_6$ haloalkyl wherein at least one methylene group is replaced with —O—, and —R$^{Si}$;

m and n are independently 0 or an integer of 1 to 6;

each R$^{Si}$ is independently an organosilicon radical; and

R is the divalent residue of an α, ω-dihydroxyl compound or an α, ω-diamino compound.

15 Claims, No Drawings

ORGANOSILICON-CONTAINING MATERIALS USEFUL FOR BIOMEDICAL DEVICES

This is a divisional of copending application Ser. No. 08/045,459 filed on Apr. 8, 1993.

BACKGROUND OF THE INVENTION

Various articles, including biomedical devices, are formed of organosilicon-containing materials. One class of organosilicon materials useful for biomedical devices, such as soft contact lenses, is silicone-containing hydrogel materials. A hydrogel is a hydrated, cross-linked polymeric system that contains water in an equilibrium state. Hydrogel contact lenses offer relatively high oxygen permeability as well as desirable biocompatibility and comfort. The inclusion of a silicone-containing material in the hydrogel formulation generally provides higher oxygen permeability, since silicone based materials have higher oxygen permeability than water.

Another class of organosilicon materials is rigid, gas permeable materials used for hard contact lenses. Such materials are generally formed of silicone or fluorosilicone copolymers. These materials are oxygen permeable, and more rigid than the materials used for soft contact lenses.

Organosilicon-containing materials useful for biomedical devices, including contact lenses, are disclosed in the following U.S. Pat. Nos.: 4,686,267 (Ellis et al.); 5,034,461 (Lai et al.); and 5,070,215 (Bambury et al.).

The present invention provides novel organosilicon-containing materials which are useful in articles such as biomedical devices, including contact lenses.

SUMMARY OF THE INVENTION

In a first aspect, the invention relates to polymers containing repeating units of formula (I):

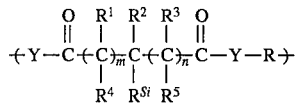
(I)

wherein:

each Y is —O— or —NR$^{30}$— wherein R$^{30}$ is H or C$_1$–C$_6$ alkyl;

each R$^1$, R$^2$, R$^3$, R$^4$ and R$^5$ is independently selected from the group consisting of H, C$_1$–C$_6$ alkyl, C$_1$–C$_6$ haloalkyl, C$_2$–C$_6$ alkyl wherein at least one methylene group is replaced with —O—, C$_2$–C$_6$ haloalkyl groups wherein at least one methylene group is replaced with —O—, and —R$^{Si}$;

m and n are independently 0 or an integer of 1 to 6;

each R$^{Si}$ is independently an organosilicon radical; and

R is the divalent residue of an α,ω-dihydroxyl compound or an α,ω-diamino compound.

In a second aspect, the invention relates to macromonomers comprising repeating units of formula (I), wherein the macromonomers are endcapped with at least one ethylenically unsaturated radical. Additionally, the invention includes monomers comprising a single unit of formula (I) endcapped with at least one ethylenically unsaturated radical. Preferred macromonomers are represented by formula (II), and preferred monomers are represented by formula (III):

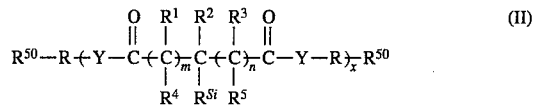
(II)

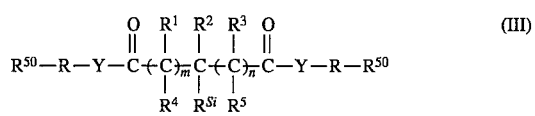
(III)

wherein each R$^{50}$ is an ethylenically unsaturated radical; each of R, R$^1$, R$^2$, R$^3$, R$^4$, R$^5$ R$^{Si}$, Y, m, and n are as defined for formula (I); and x has an average value greater than 1.

In a third aspect, the invention includes articles formed of polymer containing repeating units of formula (I). According to preferred embodiments, the article is the polymerization product of a mixture comprising the aforementioned macromonomers or monomers and a hydrophilic monomer. Preferred articles are optically clear and useful as a contact lens.

In yet another aspect, the invention relates to compounds useful as intermediates for preparing various subject polymers. These compounds have the formula:

(IV)

wherein:

each X is —OH, C$_1$–C$_6$ alkoxy or halogen; and each of R$^1$, R$^2$, R$^3$, R$^4$, R$^5$, R$^{Si}$, m, and n has the same meaning as for formula (I), provided that at least one R$^{Si}$ radical conforms to the formula:

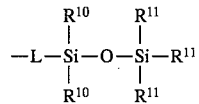

wherein each R$^{10}$ is independently selected from the group consisting of C$_1$–C$_8$ alkyl, phenyl and a group of the formula

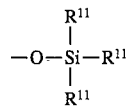

wherein each R$^{11}$ is independently selected from the group consisting of C$_1$–C$_8$ alkyl, phenyl and —O—Si(R$^{12}$)$_3$, and each R$^{12}$ is independently selected from the group consisting of C$_1$–C$_8$ alkyl and phenyl.

DETAILED DESCRIPTION OF THE INVENTION

In a first aspect, the invention relates to polymers containing repeating units of formula (I):

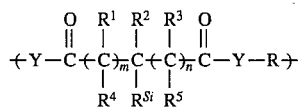

wherein:

each Y is —O— or —NR$^{30}$— wherein R$^{30}$ is H or C$_1$–C$_6$ alkyl;

each R$^1$, R$^2$, R$^3$, R$^4$ and R$^5$ is independently selected from the group consisting of H, C$_1$–C$_6$ alkyl, C$_1$–C$_6$ haloalkyl, $C_2$-$C_6$ alkyl wherein at least one methylene group is replaced with —O—, $C_2$-$C_6$ haloalkyl wherein at least one methylene groups is replaced with —O—, and —$R^{Si}$;

m and n are independently 0 or an integer of 1 to 6;

each $R^{Si}$ is independently an organosilicon radical; and

R is the divalent residue of an α,ω-dihydroxyl compound or an α,ω-diamino compound. As used herein, the term "polymer" denotes a material having an average number of repeating units of formula (I) which is greater than 1.

More specifically, the polymers include polyesters which contain repeating units of formula (Ia):

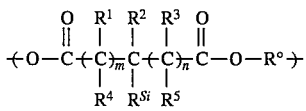
(Ia)

wherein $R^o$ is the divalent residue of an α,ω-dihydroxyl compound. Preferred polyesters include hydroxyl-endcapped polyesters of formula (Ib):

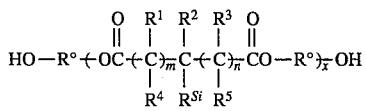
(Ib)

wherein x has an average value greater than 1.

The polymers also include polyamides which contain repeating units of formula (Ic):

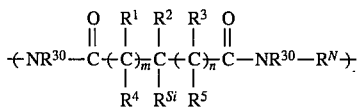
(Ic)

wherein $R^N$ is the divalent residue of an α,ω-diamino compound. Preferred polyamides include amino-endcapped polyamides of formula (Id):

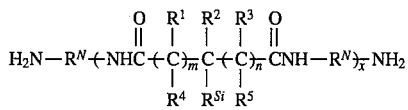
(Id)

wherein x has an average value greater than 1.

Especially preferred are polyesters or polyamides wherein each of $R^1$, $R^2$, $R^3$, $R^4$ and $R^5$ when present are hydrogen. Preferred R, $R^o$ and $R^N$ divalent radicals include: $C_1$-$C_{10}$ alkylene, $C_1$-$C_{10}$ haloalkylene such as $C_1$-$C_{10}$ fluoroalkylene, $C_2$-$C_{10}$ alkylene ethers, $C_6$-$C_{10}$ arylene, $C_6$-$C_{10}$ haloarylene, $C_7$-$C_{10}$ aralkylene, $C_7$-$C_{10}$ haloaralkylene, and $C_5$-$C_{10}$ cycloalkylene.

Preferred $R^{Si}$ radicals are organosilicon radicals of the formula:

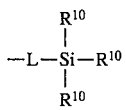

wherein each $R^{10}$ is independently selected from the group consisting of $C_1$-$C_8$ alkyl, phenyl and a group of the formula

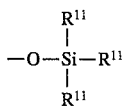

wherein each $R^{11}$ is independently selected from the group consisting of $C_1$-$C_8$ alkyl, phenyl and —O—Si($R^{12}$)$_3$, wherein each $R^{12}$ is independently selected from the group consisting of $C_1$-$C_8$ alkyl and phenyl; and L is selected from the group consisting of a single bond and a divalent linking radical.

Additionally, it is preferred that at least one $R^{Si}$ radical is a silicone-containing group of the formula:

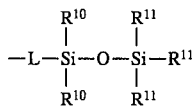

wherein each variable is as previously defined.

It will be appreciated that the L group in the above formulae links a silicon atom of the organosilicon group to the aliphatic chain in the acid moiety of the diacid or diester derivative. Preferred L groups include divalent radicals of the formula:

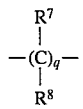

wherein q is an integer of 2 to 6, and each $R^7$ and $R^8$ is independently selected from the group consisting of H, $C_1$-$C_6$ alkyl, $C_1$-$C_6$ haloalkyl, $C_2$-$C_6$ alkyl wherein at least one methylene group is replaced with —O—, and $C_2$-$C_6$ haloalkyl wherein at least one methylene group is replaced with —O—.

Especially preferred organosilicon radicals $R^{Si}$ include: trimethylsilylethylene; pentamethyldisiloxanylmethylene; heptamethyltrisiloxanylethylene; phenyltetramethyldisiloxanylethylene; triphenyldimethyldisiloxanylmethylene; isobutylhexamethyltrisiloxanylmethylene; n-propyloctamethyltetrasiloxanylpropylene; methyl(bis[trimethylsiloxy]) silylmethylene; dimethyl(bis[trimethylsiloxy]methylsiloxanyl) silylmethylene; dimethyl(tris[trimethylsiloxysiloxanyl) silylpropylene; tris(trimethylsiloxy) silylmethylene; tris(trimethylsiloxy) silylpropylene; tris(phenyldimethylsiloxy) silylpropylene; tris(pentamethyldisiloxanyl) silylpropylene; tris[tris(trimethyldisiloxy)] silylpropylene; and tris[bis(trimethyldisiloxy)methylsiloxanyl] silylpropylene.

Various preferred $R^{Si}$ radicals may be represented by the formula:

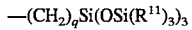

wherein each $R^{11}$ is independently selected from the group consisting of $C_1$-$C_8$ alkyl and phenyl, and q is an integer of 2 to 6.

The polyesters or polyamides containing repeating units of formula (I) may be prepared by esterification or amidation of compounds of formula (IV):

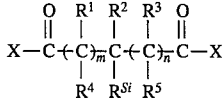
(IV)

wherein each X is —OH, $C_1$-$C_6$ alkoxy or halogen, and the remaining variables are as defined for formula (I).

As an example, polyesters of formula (Ib) may be prepared from a compound of formula (IV) and an α,ω-dihydroxyl compound by conventional polyesterification techniques according to the following general reaction scheme:

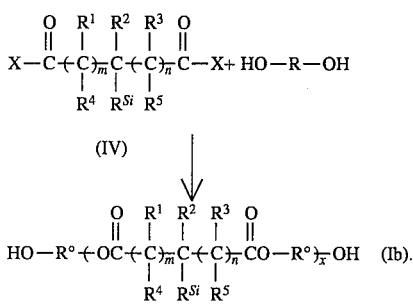

(IV)

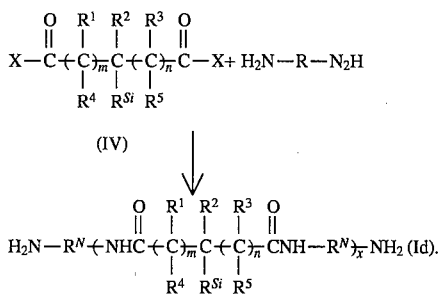

In the above reaction scheme, each X in formula (IV) is preferably a $C_1$–$C_6$ alkoxy group. $R^o$ in formula (Ib) is the residue of the α,ω-dihydroxyl compound, and corresponds to the R radical in the α,ω-dihydroxyl reactant. Representative dihydroxyl compounds include neopentyl glycol, 1,2-ethanediol, 1,6-hexanediol, triethylene glycol, bisphenol A, 1,4-cyclohexanedimethanol, 1,2-propanediol, and 2,2,3,3,4,4-hexafluoropentane-1,5-diol.

As a further example, polyamides of formula (Id) may be prepared from a compound of formula (IV) and an α,ω-diamino compound according to conventional methods as represented in the following general reaction scheme:

$$X-\underset{\underset{R^4}{|}}{\overset{\overset{O}{\|}}{C}}\text{\textendash}(C)_m\text{\textendash}\underset{\underset{R^{Si}}{|}}{\overset{\overset{R^2}{|}}{C}}\text{\textendash}(C)_n\text{\textendash}\underset{\underset{R^5}{|}}{\overset{\overset{R^3}{|}}{C}}\text{\textendash}\overset{\overset{O}{\|}}{C}-X + H_2N-R-N_2H$$

(IV)

$$H_2N-R^N+NHC\text{\textendash}(C)_m\text{\textendash}C\text{\textendash}(C)_n\text{\textendash}CNH-R^N\text{\textendash}_xNH_2 \quad (Id).$$

$R^N$ in formula (Id) is the residue of the α,ω-dihydroxyl compound, and corresponds to the R radical in the α,ω-diamino reactant. Representative diamino compounds include 1,2-ethylenediamine, 1,4-phenylenediamine, 1,6-hexamethylenediamine and 1,4-cyclohexyldiamine.

In formulae (Ib) and (Id), x has an average value greater than 1. The average number of repeating units can be varied by controlling the degree of polyesterification or polyamidation, according to known methods.

Compounds of formula (IV) may be prepared by adding an allyl group to a dicarboxylic acid, or diester thereof, containing an α,β-unsaturated group in the acid moiety via a reactive allyl silane. Representative α,β-unsaturated dicarboxylic acid or diester starting materials for this hydrosilation reaction include the following malonate derivative (Va) and succinate derivative (Vb):

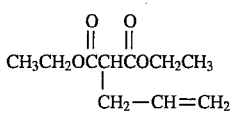

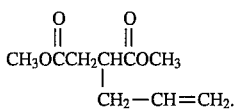

Such α,β-unsaturated dicarboxylic acids or diesters may be prepared by methods known in the art. For example, the preparation of α,β-unsaturated succinate derivative (Vb) via fluoride ion catalyzed addition of trimethylallylsilane, or via conjugate addition of lithium diallylcuprate, is described in the literature (G. Majetich et al., "A General Allylation Procedure Using Trimethylallylsilane and Fluoride Catalysts", J. Org. Chem., Vol. 51 (10), 1986, pp. 1745 et seq., the disclosure of which is incorporated herein by reference). Additionally, synthesis of α,β-unsaturated malonate derivative (Va) is described in Example 1, infra.

Accordingly, compounds of formula (IV) may be prepared according to the following general reaction scheme. For purposes of illustration in the representative reaction scheme, α,β-unsaturated malonate derivative (Va) is hydrosilated with the organosilicon $HSi(R^{10})_3$ compound to form a compound of formula (IV) containing an $R^{Si}$ radical corresponding to $-L-Si(R^{10})_3$, wherein $-L-$ is $-(CH_2)_3-$.

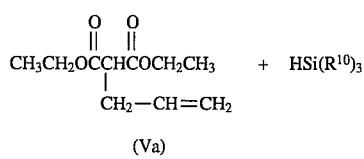

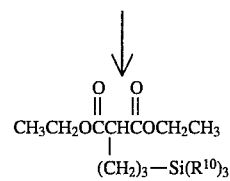

The described polyesters or polyamides containing repeating units of formula (I) may be formed directly into various shaped articles by conventional methods. However, according to preferred embodiments, shaped articles of the present invention, including contact lenses, are prepared by polymerizing a macromonomer containing repeating units of formula (I) and endcapped with at least one ethylenically unsaturated radical. Accordingly, in a second aspect, the invention relates to such macromonomers. As used herein, the term "macromonomer" denotes ethylenically unsaturated materials having an average number of repeating units of formula (I) which is greater than 1.

Preferred macromonomers include polyester-containing macromonomers endcapped with two ethylenically unsaturated radicals, as in formula (IIa):

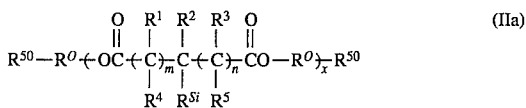

and polyamide-containing macromonomers endcapped with two ethylenically unsaturated radicals, as in formula (IIb):

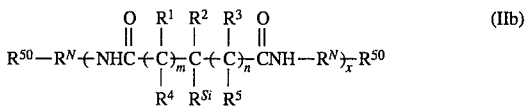

In formulae (IIa) and (IIb), each $R^{50}$ is an ethylenically unsaturated radical, and x has an average value greater than 1.

Representative $R^{50}$ radicals include ethylenically unsaturated groups of the formula:

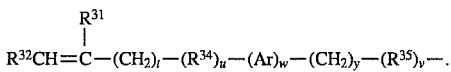

wherein:

$R^{31}$ is hydrogen or methyl;

$R^{32}$ is selected from the group consisting of hydrogen, an alkyl radical having 1 to 6 carbon atoms, and a —CO—Y'—$R^{34}$ radical wherein Y' is —O— or —NH—;

each of $R^{34}$ and $R^{35}$ is independently selected from the group consisting of —COO—, —CONH—, —NHCO—, —OCOO—, —NHCOO— and —OCONH—;

Ar is an aromatic radical having 6 to 30 carbon atoms;

each of t and y is independently 0 or an integer of 1 to 6; and each of u, v and w is independently 0 or 1.

More preferred $R^{50}$ radicals have the formula:

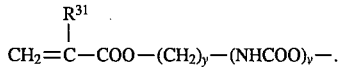

The macromonomers of the invention may be prepared by endcapping the previously described polyesters (e.g., polyesters of formula (Ib)) or polyamides (e.g., polyamides of formula (Id)) with ethylenically unsaturated groups according to general methods known in the art. Alternately, polyesters or polyamides lacking an organosilicon radical $R^{Si}$ may be endcapped with the ethylenically unsaturated group, wherein the resultant macromonomer is subsequently hydrosilated with the organosilicon radical, as illustrated in Examples 11 to 14, infra.

Various methods for adding the terminal ethylenically unsaturated group are known in the art. For example, polyesters containing terminal hydroxyl functionality, such as polyesters of formula (Ib), may be reacted with isocyanatoethylmethacrylate to form the terminal radical $CH_2=CH(CH_3)$—COO—$(CH_2)_2$—NHCOO—. Alternately, polyesters containing terminal hydroxyl functionality may be reacted with (meth)acryloyl chloride to provide a (meth)acrylate terminal radical, or with vinyl chloroformate to provide a vinyl carbonate terminal radical. Polyamides containing terminal amino functionality, such as polyamides of formula (Id), may be reacted with (meth)acryloyl chloride to provide a terminal (meth)acrylamide terminal radical, or with vinyl chloroformate to provide a vinyl carbamate end group.

It will be appreciated that be controlling the esterification or amidation, materials may be prepared which include only a single unit of formula (I). Accordingly, the invention further includes monomers containing a single unit of formula (I) endcapped with at least one ethylenically unsaturated radical. Preferred ethylenically unsaturated monomers are represented by formula (III):

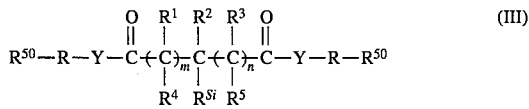

wherein each variable is as previously defined.

The resultant ethylenically unsaturated organosilicon-containing macromonomers or monomers may be polymerized by free radical polymerization to form various organosilicon-containing shaped articles, including biomedical devices. It has been found that such polymeric shaped articles have sufficiently high oxygen permeability, clarity and strength for use as contact lens materials.

For example, the macromonomers of this invention may be copolymerized with at least one hydrophilic monomer to form a hydrophilic, optically clear copolymer useful as a soft, hydrogel contact lens material. Alternately, the macromonomers may be copolymerized with monomers such as methylmethacrylate, an itaconate ester, or fluorinated derivatives thereof to form rigid, gas permeable contact lens materials.

The macromonomers may be copolymerized with a wide variety of hydrophilic monomers to form copolymers useful as hydrogel contact lens materials. Suitable hydrophilic monomers include: unsaturated carboxylic acids, such as methacrylic and acrylic acids; (meth)acrylic substituted alcohols, such as 2-hydroxyethyl methacrylate and 2-hydroxyethyl acrylate; vinyl lactams, such as N-vinyl pyrrolidone; and acrylamides, such as methacrylamide and N,N-dimethylacrylamide. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. Preferably, the macromonomer is included in the initial monomeric mixture at about 10 to about 90 percent by weight, and at least one hydrophilic monomer is included at about 10 to about 90 percent by weight.

Either the organosilicon-containing macromonomer or the hydrophilic monomer may function as a crosslinking agent (a crosslinker being defined as a material having multiple polymerizable functionalities). Alternately, a separate crosslinker may be employed in the initial monomeric mixture to provide a crosslinked polymeric article.

The monomeric mixture may be polymerized by free-radical polymerization, usually in the presence of heat or ultraviolet irradiation. Minor amounts of a free-radical initiator may be included in the monomeric mixture, generally at about 0.1 to about 5 percent by weight.

In producing contact lenses, the initial monomeric mixture may be cured in tubes to provide rod-shaped articles, which are then cut into buttons. The buttons may then be lathed into contact lenses. Alternately, contact lenses may be cast directly in molds from the monomeric mixtures, such as by spincasting and static casting methods. Spincasting methods are disclosed in U.S. Pat. Nos. 3,408,429 and 3,660,545, and static casting methods are disclosed in U.S. Pat. Nos. 4,113,224 and 4,197,266. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

The following examples illustrate various preferred embodiments of the present invention.

EXAMPLE 1

Preparation of Allyldiethylmalonate (Va)

Freshly distilled allyl bromide (13.74 g, 0.12 mol) was added at 70° C. to a solution of anhydrous ethanol containing the anion of diethylmalonate ($CH_3CH_2OOCCH^-$ $COOCH_2CH_3$, obtained by reacting allylmalonate with sodium in ethanol). The reaction was complete in two hours as determined by gas chromatography (GC). The reaction mixture was cooled, diluted with heptane (25 ml), and washed twice with distilled water. The organic extracts were dried over magnesium sulfate, and the heptane was removed with a rotoevaporator. The resultant crude product was purified by distillation to yield allyldiethylmalonate (Va) (80% yield; b.p. 115°–120° C. at 20 mmHg; purity by GC 99.0%).

EXAMPLE 2

Preparation of 2-[3-Tris(Trimethylsiloxy)Silyl)
Propyl] Diethylmalonate

Allyldiethylmalonate (8.0 g, 0.04 mol), tris(trimethylsiloxy)silane (HSi[OSi(CH$_3$)$_3$]$_3$, 11.8 g, 0.04 mol), 125 ml dry toluene and chloroplatinic acid (0.02 g in a minimum of 2-propanol) were heated at 100° C. for three hours. The reaction was monitored by GC and infrared spectroscopy. The reaction was complete in three hours. The toluene was removed with a rotoevaporator, and the crude product was vacuum distilled resulting in 2-[3-(tris(trimethylsiloxy)silyl)propyl] diethylmalonate (99.0% yield; b.p. 135°–140° C. at 0.05 mmHg; purity by GC 99.0%).

EXAMPLE 3

Preparation of Hydroxyl-Encapped Polyester from the Tris(Trimethylsiloxy)Silyl-Containing Malonate and Neopentyl Glycol 2-[3-(tris(trimethylsiloxy)silyl)propyl] diethylmalonate (10 g, 0.02 mol) and neopentyl glycol (2.5 g, 0.25 mol) were added to a round bottom flask under nitrogen. The mixture was heated to 170° C. for three hours during which time 8 ml of ethanol was distilled from the reaction mixture. The reaction mixture Was then heated to 190° C. under 30 mm of vacuum pressure for two hours. On cooling, a clear viscous polyester resulted which possessed a number average molecular weight of 3300. $^1$HNMR analysis confirmed the expected structure.

EXAMPLES 4 AND 5

Preparation of Hydroxyl-Endcapped Polyesters from the Tris(Trimethylsiloxy)Silyl-Containing Malonate and 1,6-Hexanediol or Triethylene Glycol Following the general procedure of Example 3, polyesters were prepared by substituting 1,6-hexanediol and triethylene glycol, respectively, for neopentyl glycol.

EXAMPLE 6

Preparation of Organosilicon-Containing Macromonomer from Hydroxyl-Encapped Organosilicon-Containing Polyester The hydroxyl-endcapped polyester prepared in Example 3 (5.5 g, 0.0022 mol) was dissolved in 15 ml of methylene chloride at 5° C. Isocyanatoethylmethacrylate (0.82 g, 5.28 mmol) was added slowly together with 18 µl of dibutyltindilaurate (0.3% w/w). The mixture was allowed to reach room temperature and then refluxed at 60° C. for 16 hours. The resultant mixture was washed twice with distilled water and twice with a saturated bicarbonate solution. The organic layer was collected, dried over MgSO$_4$, and the solvent was removed with a rotoevaporator. $^1$HNMR spectroscopy analysis of the final product confirmed the expected structure.

EXAMPLE 7

Preparation of Organosilicon-Containing Macromonomer

Following the general procedure of Example 6, a macromonomer was prepared from the hydroxyl-endcapped polyester of Example 5, i.e., the polyester including the residue of triethylene glycol.

EXAMPLES 8 AND 9

Casting of Films

A first mixture was prepared by mixing the macromonomer of Example 6 (80 parts by weight), N,N-dimethylacrylamide (20 parts by weight) and Darocur 1173 initiator (0.5%).

A second mixture was prepared by mixing the macromonomer of Example 7 (80 parts by weight), N,N-dimethylacrylamide (20 parts by weight) and Darocur 1173 initiator (0.5%).

Two series of films were cast from the two mixtures between glass plates by subjecting the mixtures with ultraviolet irradiation for about two hours. Following dry-release from the glass plates, the cast films were extracted overnight at room temperature in alcohol, then extracted in buffered saline, followed by hydration in phosphate-buffered saline to obtain a hydrated hydrogel. The films were clear, and properties of the films are listed in. Table 1, including percentage of water (weight %) following hydration, modulus (g/mm$^2$), tear strength (g/mm), and oxygen permeability (Dk, Barrers). Modulus and tear strength were determined by ASTM methods 1708 and 1938, and oxygen permeability was determined by the polaragraphic probe method (I. Fatt et al., International Contact Lens Clinic, Vol. 14, page 38 (1987)).

TABLE I

| Composition | % Water | Modulus | Tear Strength | Dk |
| --- | --- | --- | --- | --- |
| Example 8 | 14.6 | 275 | 7.2 | 70 |
| Example 9 | 43.6 | 122 | 1.0 | 33 |

EXAMPLE 10

Synthesis Procedure for 2-[3-(Tris[Trimethylsiloxy) Silyl)Propyl]Dimethylsuccinate, and Hydroxyl-Terminated Polyesters and Macromonomers Containing the 2-[3-(Tris(Trimethylsiloxy)Silyl)Propyl] Organosilicon Radical Following the general procedure of Example 2, 2-[3-(tris(trimethylsiloxy)silyl)propyl] dimethylsuccinate may be prepared by substituting allyldimethylsuccinate (Vb) for allyldiethylmalonate.

Hydroxyl-endcapped polyesters may be prepared by reacting 2-[3-(tris(trimethylsiloxy)silyl)propyl] dimethylsuccinate with an α,ω-dihydroxyl compound, and organosilicon-containing macromonomers may be prepared from the hydroxyl-endcapped polyesters.

EXAMPLE 11

Synthesis Procedure for Allylmalonic Acid

Potassium hydroxide (15.6 g, 0.28 mol), 15 ml of distilled water and 50 ml of heptane are added to a round bottom flask. Allyldiethylmalonate (22.0 g, 1.1 mol) is added slowly to the reaction mixture with stirring and refluxed for sufficient time to complete hydrolysis. Ethanol is removed with a rotoevaporator. The resultant product is cooled in a beaker and acidified with sulfuric acid. The final solution is extracted with diethylether. The ether layer is collected, dried over $MgSO_4$, and ether is removed with a rotoevaporator. The crude allylmalonic acid is crystalized from petroleum ether.

EXAMPLE 12

Synthesis Procedure for Amino-Endcapped Polyamide from Allylmalonic Acid and 1,6-Hexamethylenediamine Allylmalonic acid (35.3 g, 0.245 mol) and 1,6-hexamethylenediamine (34.17 g, 0.3 mol) are mixed under nitrogen in a round bottom flask equipped with a distillation head. The mixture is heated for about 2 hours at 220° C. during which time water is distilled from the reaction mixture. The reaction mixture is then heated to 250° C. under 30 mm of vacuum pressure for about three hours. The resultant mixture is cooled to yield the polyamide upon crystallization.

EXAMPLE 13

Synthesis Procedure for Ally-Containing Macromonomer from Amino-Endcapped Polyamide The amino-endcapped polyamide (5.5 g, 2.2 mmol) is dissolved in 15 ml of methylene chloride at 5° C. Isocyanatoethylmethacrylate (0.82 g, 5.28 mmol) is added slowly together with 18 μl of dibutyltindilaurate (0.3% w/w). The mixture is allowed to reach room temperature and then refluxed overnight. Subsequently, the resultant mixture is washed with distilled water and a saturated bicarbonate solution. The organic layer is collected and dried over $MgSO_4$, and the solvent is removed with a rotoevaporator.

EXAMPLE 14

Synthesis Procedure for Organosilicon-Containing Macromonomer

The methacrylate end-capped macromonomer (10 g, 0.048 mol), heptamethyldisiloxane (7.1 g, 0.48 mol) and 0.02 chloroplatinic acid is dissolved in 25 ml of ethylacetate and heated to 80° C. for sufficient time to complete the reaction, resulting in a siloxane-substituted macromonomer.

The macromonomer may be copolymerized with a hydrophilic monomer as in Examples 8 and 9.

Although certain preferred embodiments have been described, it is understood that the invention is not limited thereto and modifications and variations would be evident to a person of ordinary skill in the art.

We claim:

1. A macromonomer comprising repeating units of the formula:

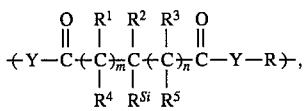

said macromonomer endcapped with at least one terminal ethylenically unsaturated radical, wherein:

each Y is —O— or —$NR^{30}$— wherein $R^{30}$ is H or $C_1$–$C_6$ alkyl;

each $R^1$, $R^2$, $R^3$, $R^4$ and $R^5$ is independently selected from the group consisting of H, $C_1$–$C_6$ alkyl, $C_1$–$C_6$ haloalkyl, $C_2$–$C_6$ alkyl wherein at least one methylene group is replaced with —O—, $C_2$–$C_6$ haloalkyl wherein at least one methylene group is replaced with —O—, and —$R^{Si}$;

m and n are independently 0 or an integer of 1 to 6;

each $R^{Si}$ is independently an organosilicon radical; and

R is the divalent residue of an α,ω-dihydroxyl compound or an α,ω-diamino compound.

2. A macromonomer of claim 1, wherein each of said at least one terminal ethylenically unsaturated radical is independently a radical of the formula:

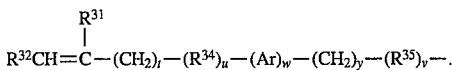

wherein:

$R^{31}$ is hydrogen or methyl;

$R^{32}$ is selected from the group consisting of hydrogen, an alkyl radical having 1 to 6 carbon atoms, and a —CO—Y'—$R^{34}$ radical wherein Y' is —O— or —NH—;

each of $R^{34}$ and $R^{35}$ is independently selected from the group consisting of —COO—, —CONH—, —NHCO—, —OCOO—, —NHCOO— and —OCONH—;

Ar is an aromatic radical having 6 to 30 carbon atoms;

each of t and y is independently 0 or an integer of 1 to 6; and each of u, v and w is independently 0 or 1.

3. A macromonomer of claim 2, wherein said macromonomer is endcapped with two ethylenically unsaturated radicals.

4. A macromonomer of claim 2, wherein each of said at least one ethylenically unsaturated radicals is independently a radical of the formula:

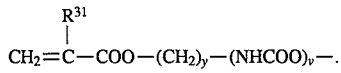

5. A macromonomer of claim 1, wherein each Y is —O—.

6. A macromonomer of claim 1, wherein each Y is —$NR^{30}$—.

7. A macromonomer of claim 1, wherein R is selected from the group consisting of $C_1$–$C_{10}$ alkylene, $C_1$–$C_{10}$ haloalkylene, $C_2$–$C_{10}$ alkylene ethers, $C_6$–$C_{10}$ arylene, $C_6$–$C_{10}$ haloarylene, $C_7$–$C_{10}$ aralkylene, $C_7$–$C_{10}$ haloaralkylene, $C_5$–$C_{10}$ cycloalkylene and $C_6$–$C_{12}$ alkylcycloalkylene.

8. A macromonomer of claim 1, wherein m is 0 and n is 0 or 1.

9. A macromonomer of claim 1, wherein each $R^{Si}$ is an organosilicon radical of the formula:

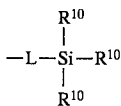

wherein each $R^{10}$ is independently selected from the group consisting of $C_1-C_8$ alkyl, phenyl and a group of the formula

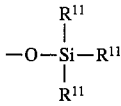

wherein each $R^{11}$ is selected from the group consisting of $C_1-C_8$ alkyl, phenyl and $-O-Si(R^{12})_3$, and each $R^{12}$ is independently selected from the group consisting of $C_1-C_8$ alkyl and phenyl; and each L is independently a divalent linking radical.

10. A macromonomer of claim 9, wherein each L is independently a divalent linking group of the formula:

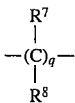

wherein:

q is an integer of 2 to 6; and $R^7$ and $R^8$ are independently selected from the group consisting of H, $C_1-C_6$ alkyl, $C_1-C_6$ haloalkyl, $C_2-C_6$ alkyl wherein at least one methylene group is replaced with $-O-$, and $C_2-C_6$ haloalkyl wherein at least one methylene group is replaced with $-O-$.

11. A macromonomer of claim 1, containing repeating units of the formula:

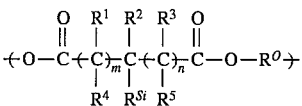

(Ia)

wherein $R^o$ is the divalent residue of an $\alpha,\omega$-dihydroxyl compound.

12. A macromonomer of claim 11, wherein $R^{Si}$ is

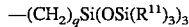

wherein each $R^{11}$ is independently selected from the group consisting of $C_1-C_8$ alkyl and phenyl, and q is an integer of 2 to 6.

13. A macromonomer of claim 1, having the formula:

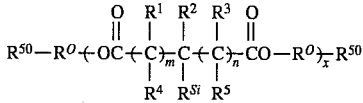

wherein $R^{50}$ is an ethylenically unsaturated radical, $R^o$ is the divalent residue of an $\alpha,\omega$-dihydroxyl compound, and x has an average value greater than 1.

14. A macromonomer of claim 1, having the formula:

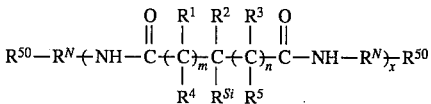

wherein $R^{50}$ is an ethylenically unsaturated radical, $R^N$ is the divalent residue of an $\alpha,\omega$-diamino compound, and x has an average value greater than 1.

15. A monomer having the formula:

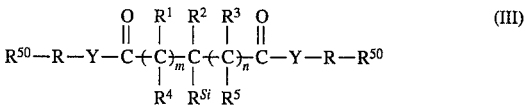

(III)

wherein:

each Y is $-O-$ or $-NR^{30}-$, wherein $R^{30}$ is H or $C_1-C_6$ alkyl;

each $R^1$, $R^2$, $R^3$, $R^4$ and $R^5$ is independently selected from the group consisting of H, $C_1-C_6$ alkyl, $C_1-C_6$ haloalkyl, $C_2-C_6$ alkyl wherein at least one methylene group is replaced with $-O-$, $C_2-C_6$ haloalkyl wherein at least one methylene group is replaced with $-O-$, and $-R^{Si}$;

m and n are independently 0 or an integer of 1 to 6;

each $R^{Si}$ is independently an organosilicon radical;

R is the divalent residue of an $\alpha,\omega$-dihydroxyl compound or an $\alpha,\omega$-diamino compound; and $R^{50}$ is an ethylenically unsaturated radical.

* * * * *